United States Patent [19]
Le Beux et al.

[11] Patent Number: 6,128,400
[45] Date of Patent: Oct. 3, 2000

[54] AUTOMATIC EDITING METHOD FOR A DIGITAL MEDICAL IMAGING UNIT AND A UNIT FOR IMPLEMENTING THE METHOD

[75] Inventors: Jean-Claude Le Beux, Vincennes; Jean-Marie Vau, Paris, both of France

[73] Assignee: Eastman Kodak Company, Rochester, N.Y.

[21] Appl. No.: 09/004,016

[22] Filed: Jan. 7, 1998

[30] Foreign Application Priority Data

Feb. 3, 1997 [FR] France .................................. 97 01510

[51] Int. Cl.⁷ .................................................. G06K 9/00
[52] U.S. Cl. .......................................................... 382/132
[58] Field of Search .................................. 382/128, 132, 382/298, 305, 306; 345/438, 439; 378/62, 98; 358/1.2, 1.5, 1.12

[56] References Cited

U.S. PATENT DOCUMENTS

| 5,544,215 | 8/1996 | Shroy et al. | 378/98.12 |
| 5,734,915 | 3/1998 | Roewer | 707/512 |
| 5,806,521 | 9/1998 | Morimoto et al. | 600/447 |

FOREIGN PATENT DOCUMENTS

| 0 632 400 A2 | 1/1995 | European Pat. Off. . |
| 0 632 400 | 4/1995 | European Pat. Off. . |

OTHER PUBLICATIONS

Wong, S.T.C. et al., "A Hospital Integrated Framework for Multimodality Image Base Management," IEEE Transactions on Systems, Man and Cybernetics. Part A: Systems and Humans, vol. 26, No. 4, Jul. 1, 1996, pp. 455–469.

Stephen T. C. Wong and H. K. Huang Man and Cybernetics—Part A: Systems and Humans "A Hospital Integrated Framework for Multimodality Image Base Management" Jul 1996 vol. 26, No. 4 pp. 455–469.

*Primary Examiner*—Joseph Mancuso
*Assistant Examiner*—F. E. Cooperrider
*Attorney, Agent, or Firm*—William F. Noval

[57] ABSTRACT

The invention relates to the editing of digital medical images.

A digital medical imaging unit normally comprises: a station 10 for entering information relating to a patient Id, a scanner 20 for scanning first medical image media and associated with a means 16, 18, 19 of entering information relating to the medical examination to be processed, an editing station 30 designed to send the digital images to be edited to a printer 50. The only known automatic editing system consists of editing each digital image as soon as they are delivered by the scanner 20 on individual pages of an editing medium. The unit according to the invention comprises on the one hand an editing controller 40 which receives, before the processing of a first medical image medium, information relating to the editing, and on the other hand a counter of medical images processed by the scanner.

Application to the automatic editing of several digital medical images on one and the same page of an editing medium.

8 Claims, 13 Drawing Sheets

35x43  20x25  28x35

Edit the images without stopping filling the page

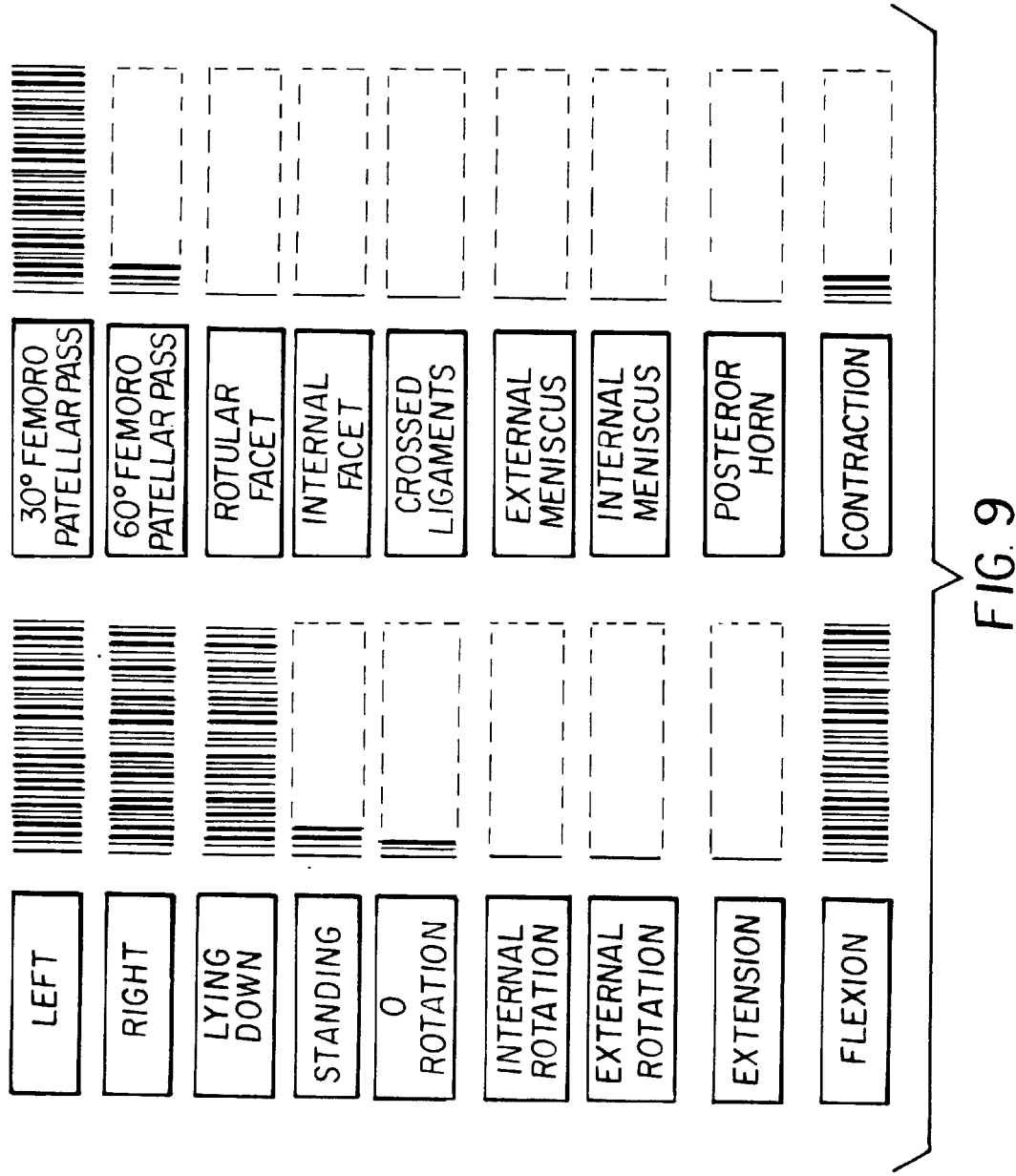

AUTOMATIC EDITING METHOD FOR A DIGITAL MEDICAL IMAGING UNIT AND A UNIT FOR IMPLEMENTING THE METHOD

FIELD OF THE INVENTION

The present invention relates to the editing of digital radiographic images and more particularly to the automated deferred editing of such images.

BACKGROUND OF THE INVENTION

The field of medical radiography has undergone profound changes in the past few years. In particular, the development of new types of recording media using photoluminescent memory plates, well known by the name of "phosphor plates", has enabled digital medical imaging to be developed. Traditionally, radiographic images were obtained on photosensitive plates which, after processing in photographic treatment baths, enabled the radiographic image to be displayed. Technological developments in the past few years with regard to image processing have made it possible to envisage obtaining radiographic images which can be exploited from digital data.

A digital medical imaging unit is associated with a radiography system using "phosphor cartridges", that is to say cartridges provided with photoluminescent memory plates used to form a latent analogue radiographic image.

In order to be able to exploit the latent image contained in the photoluminescent memory plate, the cartridge is inserted into a reading device in which the plate is extracted from the cartridge and then scanned with a reading beam so as to excite the plate locally. This excitation causes a photoluminescent emission which is a function of the irradiation received by the plate. By means of a photosensitive sensor, the reading device converts the intensity of the radiation emitted by the plate into an analogue electrical signal which is then converted into digital data. By scanning the plate, the reading device therefore supplies, for each plate, a digital representation of the information carried by the photoluminescent memory plate. The reading device is very often associated with an automatic cartridge dispenser enabling a plurality of cartridges to be disposed at the entry to the reading device. After the processing of a cartridge by the reading device, the latter erases any residual information on the plate and returns the cartridge to the dispenser and takes therefrom a new cartridge in order to process it.

The digital representation coming from the reading device is then processed by a suitable digital processing unit provided with distinct processing algorithms dependent on the type of radiographic images recorded on the photoluminescent memory plate. To do this, information relating to the type of radiographic examination carried out with the cartridge concerned is supplied to the processing unit.

The medical imaging unit also comprises a workstation which, after receipt of the digital medical images, makes it possible to edit the various images contained in the memory of the processing unit.

A description will now be given of the conventional use of a digital medical imaging unit. When it is desired to carry out a radiographic examination of a patient by means of a digital medical imaging unit, the information required for the identification of the patient is first of all introduced into the computer. In general the surname of the patient and his first name are introduced, sometimes his sex and his age. A unique identification number, which can be coded and printed in the form of a bar code on labels, is made to correspond to this information. Normally, each phosphor cartridge is identified unequivocally in order to be able to be recognized by the processing unit. In one particularly advantageous embodiment, the cartridges are identified by means of a bar code. During the radiographic examination it is necessary to introduce into the processing unit the type of examination recorded in each cartridge. Advantageously, in some medical imaging units, this information can be introduced into the processing unit by means of a bar code reader, preferably portable, which will capture the information directly at the time of the radiographic examination. In this way any possible mixing up of the cartridges is avoided when the examination requires more than one cartridge for the patient.

In a particularly advantageous known embodiment, at the time of exposure to x-rays, there are entered with a bar code reader, preferably portable, of the code of the patient, the code of the cartridge, the type of examination or part of the patient observed (cranium, thorax, shoulder, hand, etc), the type of projection (side, profile, antero-posterior or AP, postero-anterior or PA), the orientation (landscape, portrait) with a view to the correct display on the screen or at the time of editing and optionally the position of the patient (lying down, standing, semi-seated), the name of the person carrying out the examination and the technical data (kV, mAS, distance). Once the data have been entered, a validation data item or End is sent to the processing unit.

After the exposure of the cartridges to x-rays and the recording, in the processing unit, of the data relating to the examinations, the cartridges are inserted in the automatic dispenser associated with the reading device so as to obtain a digital representation of each of the radiographic images recorded in each of the cartridges.

By means of the information entered relating to each exposure, the processing unit applies the appropriate processing algorithms to the digital information and associates a patient with each of the cartridges.

Then, using a workstation, an operator is able to edit, on an editing medium, one after the other, the various images contained in the processing unit. In an automatic operating mode of the workstation, the printer produces one image from the processing unit per page of the editing medium as the processing unit delivers a processed digital image. Advantageously, provision can be made for the dimension of the editing medium to be determined by default either by the size of the cartridge or by the type of examination.

For certain types of examination, it is desirable to group together several radiographs on a single editing page. To do this, an operator manually controls the workstation in order to associate, with one and the same page of an editing medium, the digital images to be edited on this page. This type of editing requires human intervention. An operator must, before commencing the editing of several images on a single medium, verify that all the digital images are available. If the images to be edited are not all available, the operator must either wait until all the images are available or subsequently recommence the entry relating to the editing. These operations are tedious and take up time, and there is a risk of transposing certain radiographs.

SUMMARY OF THE INVENTION

The present invention aims to provide a digital medical imaging unit which does not present the drawbacks mentioned above.

The present invention also aims to provide a digital medical imaging unit in which the operator is able to indicate, before the conversion of the radiographic image into a digital image, the type of editing required for the radiograph contained in a cartridge, in order to automate the final editing in the desired form, thus avoiding the subsequent intervention of an operator.

BRIEF DESCRIPTION OF THE DRAWINGS

Other advantages and objects of the invention will emerge from a reading of the following description given by way of example and made with reference to the accompanying drawing in which:

FIG. 9 depicts a few possible labels which can be overlaid on the images received from the reading device.

DETAILED DESCRIPTION OF THE INVENTION

Figure 1:
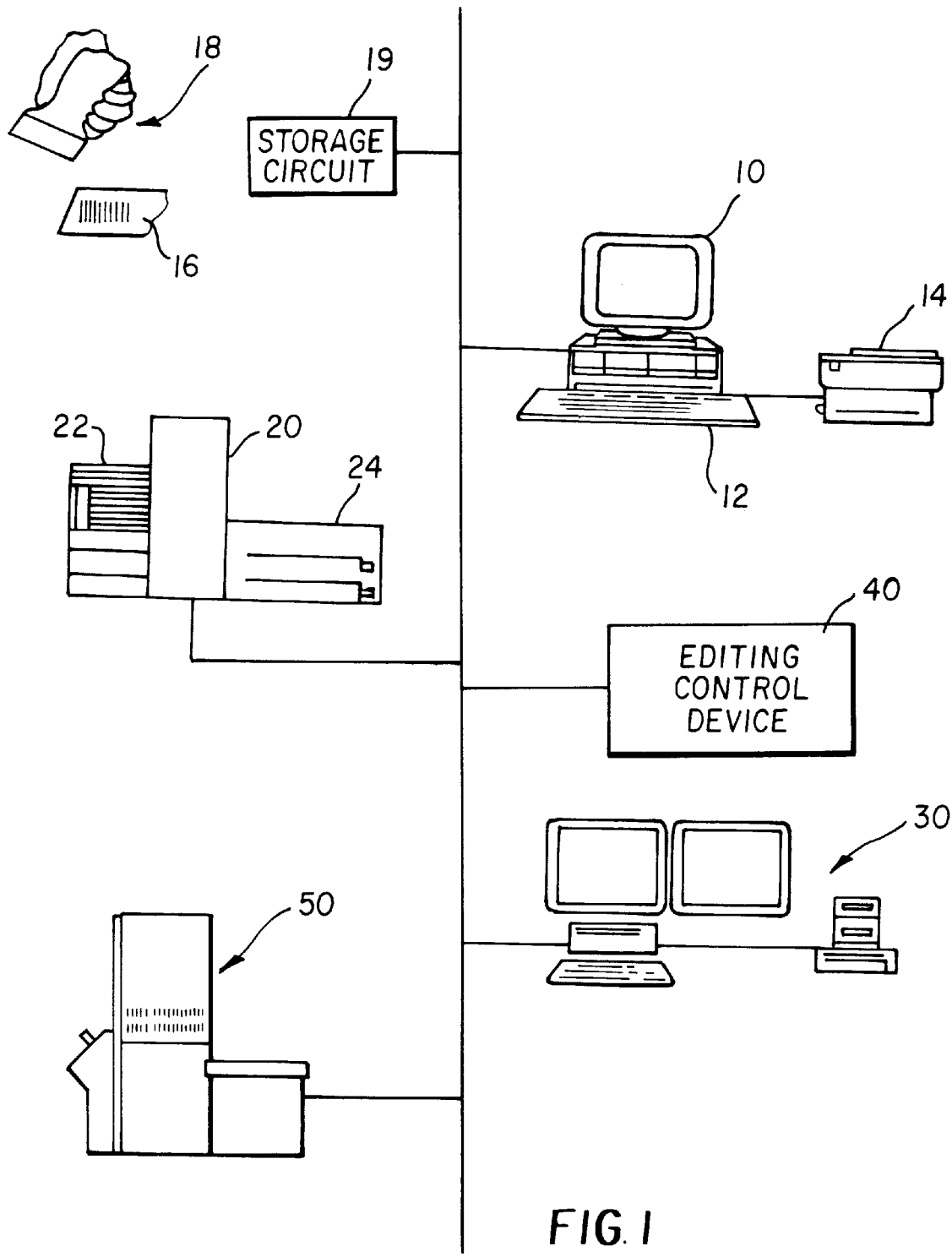
FIG. 1 depicts diagrammatically a possible architecture for a medical imaging unit.

FIG. 1 depicts diagrammatically the elements of a medical digital imaging unit and more particularly the logic connections necessary to such a unit. A digital medical imaging laboratory comprises, in addition to the apparatus for irradiating the media for recording the radiographic image, a digital medical imaging unit. In such laboratories, the recording media consist of photoluminescent memory plates disposed in cartridges. As in traditional radiography, there are several plate formats and several cartridge formats.

As can be seen in FIG. 1, the medical imaging unit comprises an entry station 10, for example a personal computer, provided with a keyboard 12 and a printer 14 advantageously making it possible to edit information in the form of bar codes. The entry station 10 is used at the start of an examination to introduce the data relating to the patient and necessary for an interpretation of the images which will be edited. These data generally comprise the identity of the patient: his surname and first name and optionally his age or date of birth, his sex or other information. A unique code is associated with the data relating to the patient so as to cause each image to correspond unequivocally to a single patient (even when there are patients having identical surnames and first names). Advantageously, the code associated with the patient is converted into a 16-bar code which can be read by means of a data capture device 18 such as for example a bar code reader, known commercially. The reader 18 transmits the information contained in the bar code to a storage circuit 19 so as to be able to be used subsequently by the other components of the digital medical imaging unit.

The digital medical imaging unit also comprises a device 20 for reading the recording media on which a radiographic image of the patient has been formed. This device, known per se, can be the one sold under the commercial name "Kodak Digital Science Model 400 Digital Radiology System with Photoluminescent Screens" by the Eastman Kodak Company or any other equivalent device. Advantageously, the reading device 20 can be associated with an automatic feed dispenser 22 in which up to around ten cartridges, which will be processed successively by the reading device 20, can be inserted simultaneously. As is well known, the reading device is provided with a light source of the laser type, a scanning device enabling the laser beam to be moved along the photoluminescent plate which has been exposed to x-rays and a photosensitive detector for receiving the radiation emitted by the plate under the effect of the excitation supplied by this laser beam. The reading device 20 is associated with a processing unit 24 which comprises various image processing algorithms in order to improve the digital image supplied by the photosensitive detector. Each type of examination being associated with a given algorithm, it is necessary to associate, before the reading of a plate, the plate and the type of examination which has been recorded on this plate. Advantageously, this association is possible by virtue of the information transmitted to the circuit 19 for example by the bar code reader 18, preferably portable. The type of information to be entered is depicted for example in FIG. 2. Such a bar code reader makes it possible to enter, at the time of examination, the data necessary to the processing unit in order to provide a correct digital medical image. Advantageously, as is known, the bar codes representing the information to be entered comprise in their coding the type of information which they represent. For example, the codes relating to patients are preceded by the letter P, the codes for the cartridges are preceded by the letter C, the codes relating to the examinations are preceded by the letter E, etc. In this way, it is possible to enter the information in any order. In addition, if it is desired to modify an item of information, the entry of a new item of information of the same type automatically replaces the previous entry.

The digital medical imaging unit also comprises an editing station 30 provided with at least one display screen, a keyboard and optionally a mouse. This workstation transmits the images to be edited to a laser printer 50. Such an editing station is known commercially. It is offered by the company Kodak-Pathé under the name MasterPage workstation. Obviously any other similar device may be used. The editing station makes it possible, by means of suitable software, to associate several images on the same page of an editing medium contained in the printer 50, and to print them with this printer. In the preferred embodiment used with the invention, the printer is sold by the Eastman Kodak Company under the trade name "Kodak Ektascan 2180 Laser Imager" and the editing medium is a black and white film of the Kodak Ektascan type.

According to the invention, the processing unit 24 is also provided with an automatic editing control device 40. This control device, which can be in the form of a program, makes it possible to provide the editing station 30 with the information for automatically editing the images relating to a patient. The automatic editing control device 40 uses the information transmitted by the circuit 19 and relating to editing.

Figure 3:
FIG. 3 depicts a possible chart useful to the implementation of the invention.
Figure 3:
Figure 3:
Figure 3:
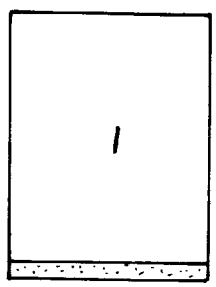
Figure 3:
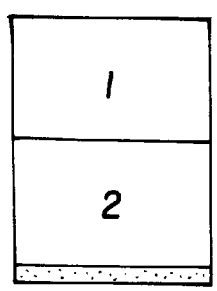
Figure 3:
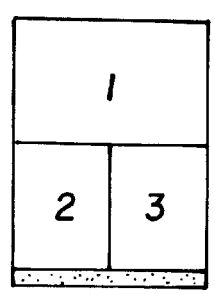
Figure 3:
Figure 3:
Figure 3:
Figure 3:
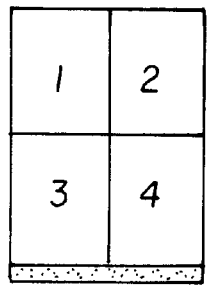
Figure 3:
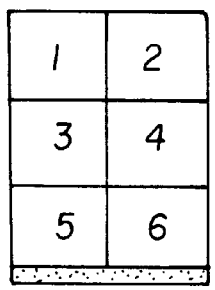
Figure 3:
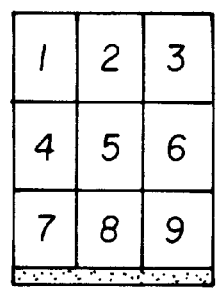
Figure 3:
Figure 3:
Figure 3:
Figure 3:

The information necessary to the editing station comprise first of all an indication relating to the editing medium format, which is chosen from amongst the three formats provided for the laser printer 50, for example 35'43, 20'25 or 28'35, and then information relating to an editing template or box chosen from amongst a template set depicted for example in FIG. 3. Obviously other types of template other than those provided in this figure can be designed and programmed according to the most usual examinations used in the medical imaging laboratory.

Figure 2:
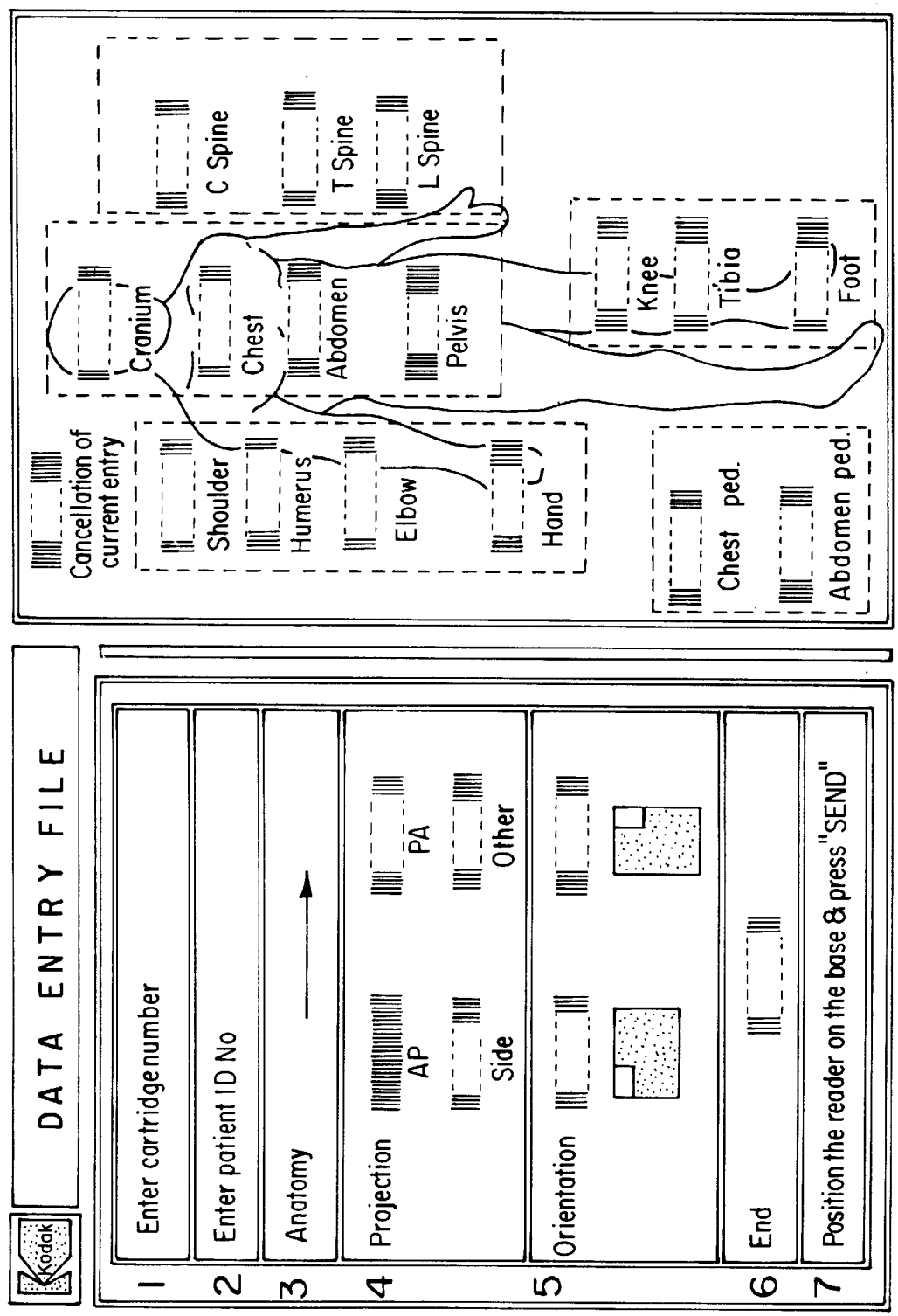
FIG. 2 depicts a known possible chart for easily entering the information useful to the processing of the image.

After entering the usual information depicted in FIG. 2, the information relating to the size of the editing medium to be used (see FIG. 3) is entered with the bar code reader. Then, before the insertion of the cartridge into the reading device, the information relating to the editing template (FIG. 3) which will be used during editing is entered.

In a specific embodiment, the storage circuit 19 forms an integral part of the reading device 20. This is the case with the device mentioned above and called the "Kodak Digital Science Model 400 Digital Radiology System with Photoluminescent Screens" from the Eastman Kodak Company. In this specific embodiment, the editing control device 40 forms an integral part of the MasterPage workstation. The invention as described with reference to FIGS. 4 or 5 applies to this type of installation. However, it is clear that it is possible to design another type of installation in which the storage circuit 19 is independent of the reading device 20 and transmits the information on the one hand to the reading device 20 at the moment when the latter identifies a cartridge in the course of scanning or processing and on the other hand to the editing control device 40, which is completely independent, at the moment when a digital image is supplied by the reading device.

The digital image supplied by the reading device 20 comprises on the one hand a header in which are found the information entered by the bar code reader and on the other hand the image itself. In the header there are not only the codification of the digital image but also the information entered and more particularly the orientation of the image (portrait or landscape), the time when the information was entered, the format of the editing support (35'43, 20'25, 28'35) and the number of radiographic images to be edited on one and the same page of the editing medium.

Figure 4A:
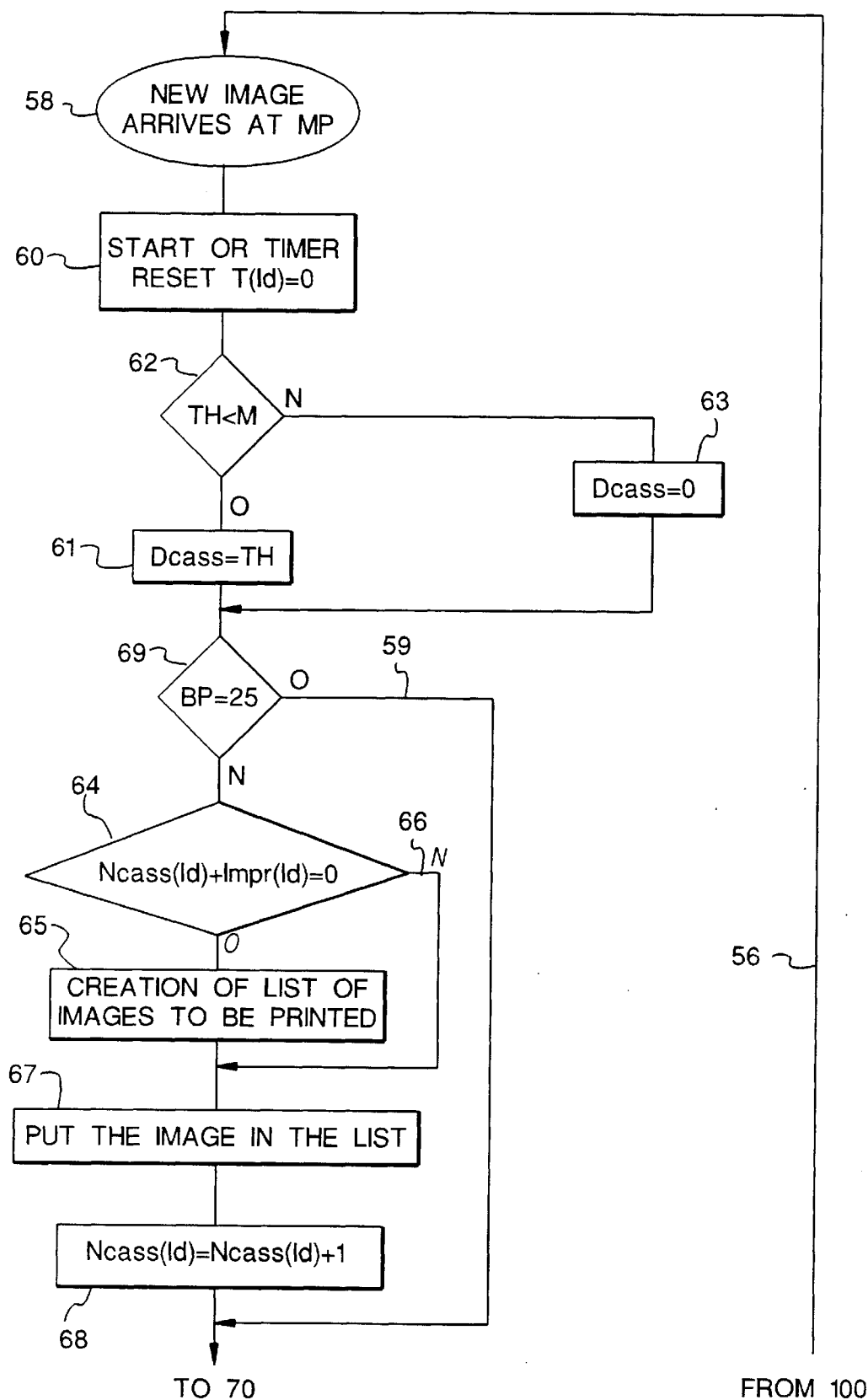
FIGS. 4A to 4C depict diagrammatically the operating flow chart of an automatic editing control device.
Figure 4B:
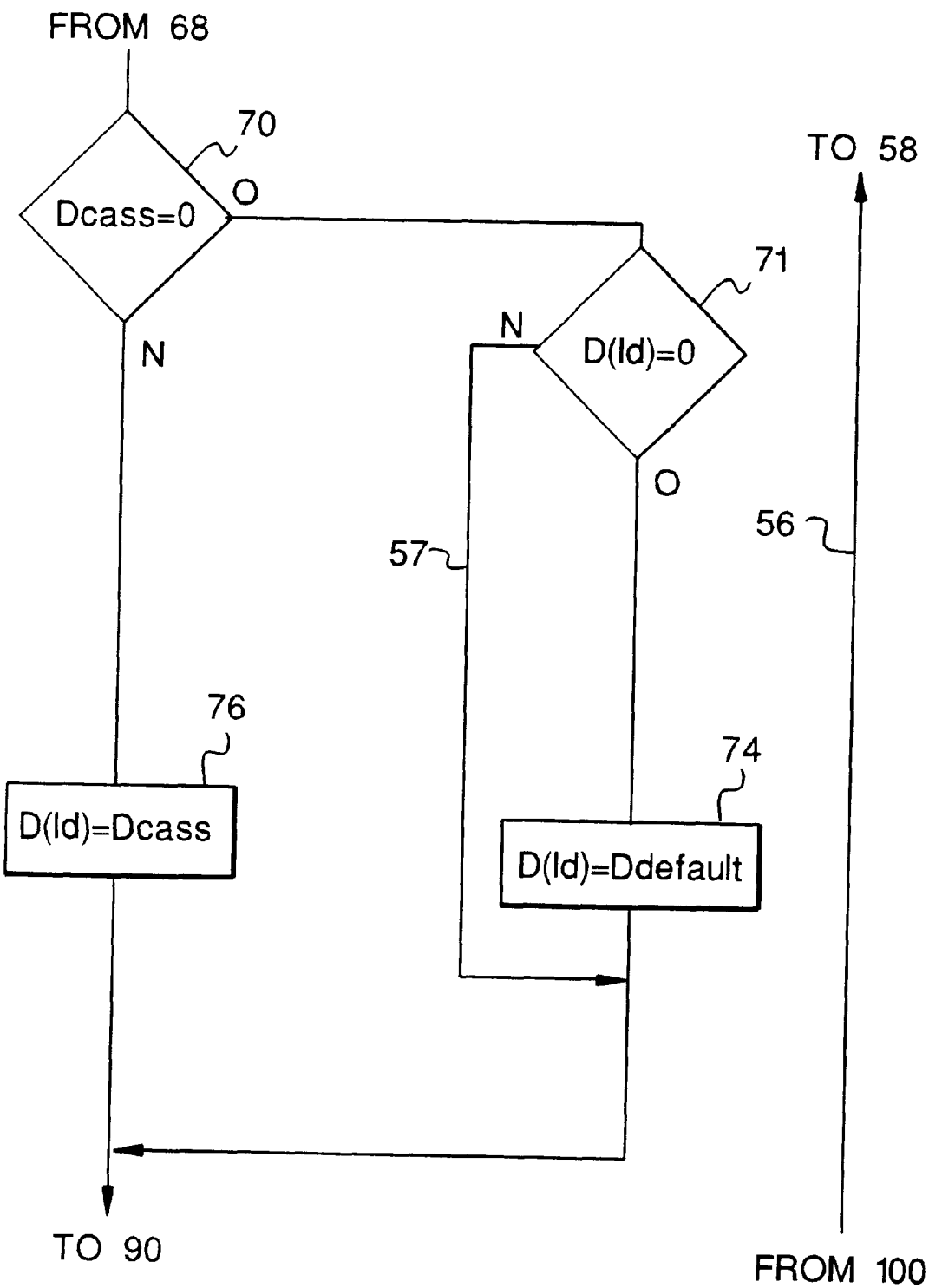

The embodiment described with reference to FIGS. 4A to 4C relates to a digital medical imaging unit in which the information corresponding to FIGS. 2 and 3 must be introduced into the unit in order of their entry. When the digital medical imaging unit is started up, all the temporary recording areas are set to zero. At each reception at 58 of a digital image, coming from the reading device 20, the automatic editing control device 40 resets to zero, at 60, a time counter T(Id) which contains the period of time since which the automatic editing control device 40 has received an image corresponding to the same patient. The use of this counter will be described subsequently. The automatic editing control device 40 seeks, in an area TH of the header, the number of images to be edited on the same page of the editing support. This number is entered at 61 in an area Dcass. For reasons of memory space problems, it is possible to use an existing area TH of the header normally containing another item of information of a different identifiable type; for example an alphabetical information item with respect to a numerical information item, a numerical information item lower than a normal minimum value contained in the area, an information item preceded by a specific control character, or any other type of distinction. In the particular case described in FIG. 4, the information item is a numerical value less than a given value M. The automatic editing control device 40 therefore comprises a test 62 for verifying that the information contained in the area TH does indeed correspond to the number of images desired per page of editing medium. In this case the automatic editing control device 40 introduces at 61 the value of TH in the area Dcass. Where the operator has not entered the number of images to be arranged on the same page, the area TH contains another type of information and the test 62 is negative. In such case, the automatic editing control device 40 introduces at 63 a zero value in the area Dcass and avoids the operation 61.

An area Ncass(Id) contains the number of cartridges which have been read by the reading device 24 and which relate to the patient Id. An area Impr(Id) contains the number of edited pages corresponding to a patient Id. When the digital medical imaging unit is started up the area Ncass(Id) is set to zero as well as the area Impr(Id).

After having given information to the area Dcass at 61 or at 63, the automatic editing control device 40 tests at 64 the value Ncass(Id)+Impr(Id). This value is zero only when the automatic editing control device 40 tests the first image relating to the patient Id. When this value is zero, the automatic editing control device 40 creates at 65, for the patient Id, the list of images to be printed. When the value Ncass(Id)+Impr(Id) is different from zero, the automatic editing control device 40 avoids the creation of the list at 35 by passing through the connection 66. Then the automatic editing control device 40 introduces at 67 the digital image in the list of images to be edited and then adds at 68 one unit to the area Ncass(Id).

There is provided, in the header of the file corresponding to each image, an area BP in which a given value is introduced, for example 25, when the reading device has determined that an image could not be edited. A test 69 verifies the value of the area BP. When the test 69 detects an image which it is not desired to edit, the operations 64 to 68 are avoided by passing through the path 59.

After having updated at 68 the number of images received by the automatic editing control device 40, the content of the area Dcass is tested at 70. When the first image reaches the automatic editing control device 40, the value contained in the area Dcass is not generally zero.

If Dcass is different from zero the value of Dcass is put in an area D(Id) representing, for the patient Id, the number of images which it is desired to edit per page of the editing support. If Dcass is zero, which corresponds to the operator having forgotten to indicate, at the time of recording of the first cartridge, the number of images to be edited per page of editing medium, the automatic editing control device 40 checks at 71 whether the template or box D(Id) chosen for the patient is zero. When this value D(Id) is zero, corresponding solely to the passage of the first image, there is introduced at 74 in the area D(Id) a default value which can be equal to any value and which may depend on the type of examination indicated in the header of the file transmitted by the reading device 20. This default value can be contained in a table which the automatic editing control device 40 will be able to consult. When D(Id) is different from zero and Dcass is zero, the automatic editing control device 40 does not modify this value by taking the path 57, thus avoiding the operation 74.

When the reading device 20 delivers an image relating to a cartridge for which a number of images to be edited per page of editing medium has been entered, the content of the area TH has been copied into the area Dcass at 61. The test 70, being therefore negative, controls at 74 the introduction of the value of Dcass into D(Id). This function optionally makes it possible to modify, during operation, the number of images edited per page of editing medium. It will be noted that this modification is retroactive only on the images which have not been edited.

The automatic editing control device 40 then tests at 90 the value of Ncass(Id)–D(Id) in order to check whether the number of images received is able to fill a page of the editing medium in accordance with the wishes of the operator. When the value Ncass(Id)–D(Id) is positive or zero a page can be edited by the function A, which will be described subsequently. After editing, the edited images are eliminated at 91 from the list of images to be printed given at 67, the page counter Impr(Id) is incremented at 92 by one unit, and the number of cartridges Ncass(Id) read and given at 68 is decremented at 93 by the number of images printed D(Id). The automatic editing control device 40, by virtue of the path 94, once again tests at 90 the value Ncass(Id)–D(Id) in order to check whether the number of images received and remaining to be printed is able to fill a new page of the editing medium.

Advantageously, a specific code makes it possible to edit all the images awaiting editing. In the embodiment depicted, this specific code corresponds to a value of 15 for the area D(Id).

When the number of images is insufficient, the automatic editing control device 40 then tests at 100 whether the value is less than or equal to the specific code (for example 15). In cases where the value of D(Id) is strictly less than the value given, the digital medical imaging unit returns to the path 56 in order to await the next image at 58 and recommence the cycle. In cases where the test 100 is negative, the automatic editing control device 40 returns to the printing A of the images.

Advantageously, the automatic editing control device 40 comprises an automatic editing triggering module. In order to avoid keeping in memory, without editing, an image relating to a patient Id, the automatic editing control device 40 continuously compares at 110 the value of the time counter 60 with a maximum value Tmax so as to trigger the editing of the images when the digital medical imaging unit has not received any images relating to a given patient Id for a period equal to Tmax. In the preferred embodiment, the value of Tmax is around 10 minutes. When T(Id) is greater than or equal to Tmax, the automatic editing control device 40 sends a signal which at 111 tests the value of Ncass(Id) compared with zero. If Ncass(Id) is equal to zero, the images relating to the patient Id have all been edited. In this case the automatic editing control device 40 resets to zero all the parameters relating to the patient Id and closes the list of images to be printed created at 65. This operation enables the code Id to be used once again for another patient. If Ncass (Id) is different from zero, there are still images to be edited. In such a case, the number of images remaining to be edited is introduced at 113 into the area D(Id) and the information is sent to the editing module A.

Figure 6:
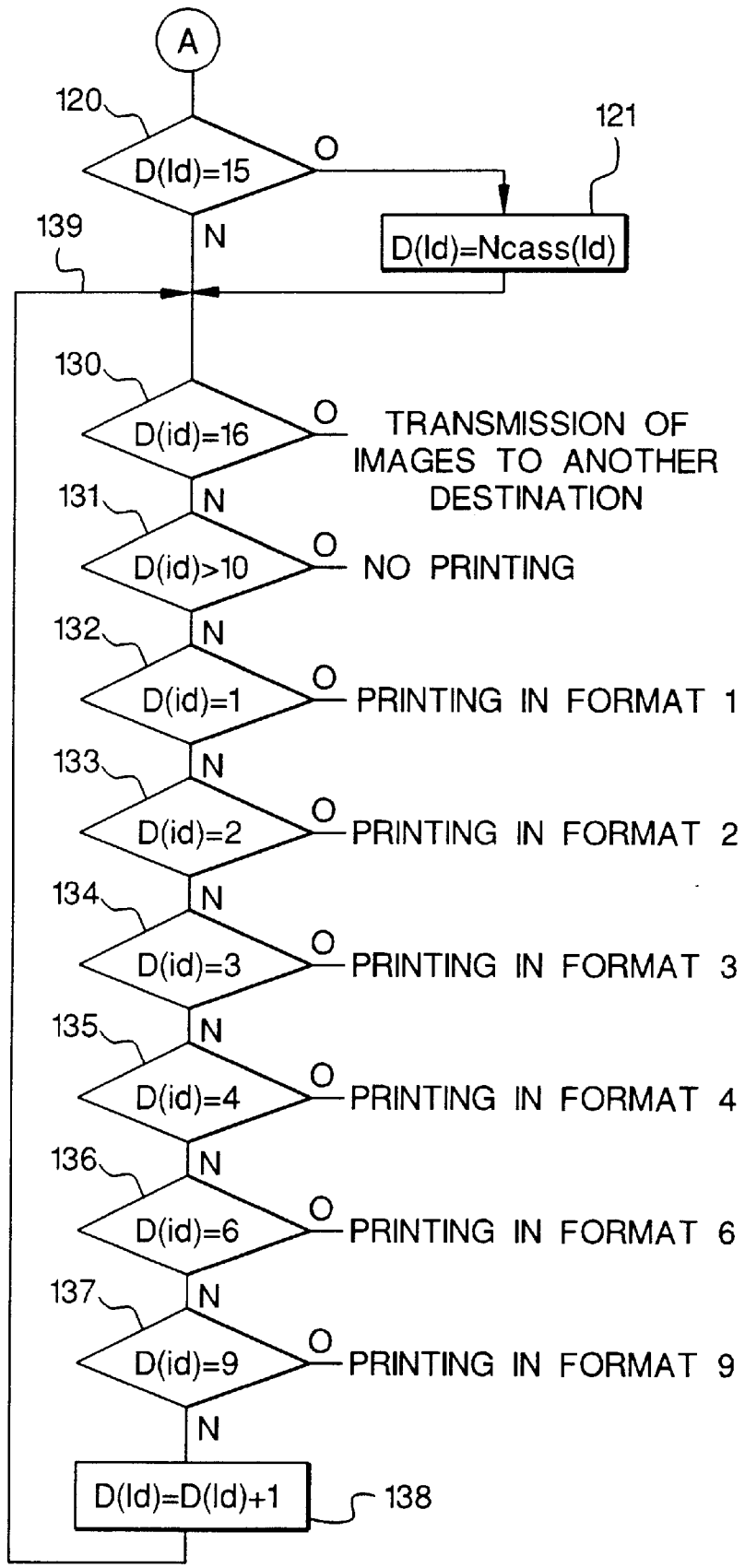
FIG. 6 depicts diagrammatically a possible flow chart for an editing module which can be used according to the invention.

A description will now be given of the editing module A with reference to FIG. 6. First of all the value of D(Id) is tested at 120. If this is equal to the specific code, for example 15, this indicates that the immediate editing of all the images which have not yet been edited relating to the patient Id is required. In this case, the number of images Ncass(Id) remaining in the list to be edited is introduced at 121 into the area D(Id). When D(Id) is different from 15, this value of D(Id) is not modified. This value is compared in turn, at 130 to 137, with different values so as to trigger the printings by modules enabling a specific number of images to be edited on the same page of an editing medium. In order to ensure that the images are edited in all cases, after having passed before all the tests 130 to 137 and if the value of D(Id) has not been detected, the area D(Id) is incremented by one unit at 138 and then, by means of the path 139, all the tests 130 to 137 are recommenced. In a particularly advantageous embodiment a value equal to 16 enables all the images to be transmitted without editing them to another destination. In another embodiment, by modifying the test 130 in order to put therein the inequality $D(Id)^3 16$, it is possible to choose, through the specific value of D(Id), one destination amongst a possible set of destinations. As can be seen, a set of five images will be edited on a page which can include six images and a set of seven or eight images will be edited on a page able to include nine images. The various printing modules associated with each of the tests 132 to 137 have not been described in more detail since the programming can easily be effected.

Figure 8:
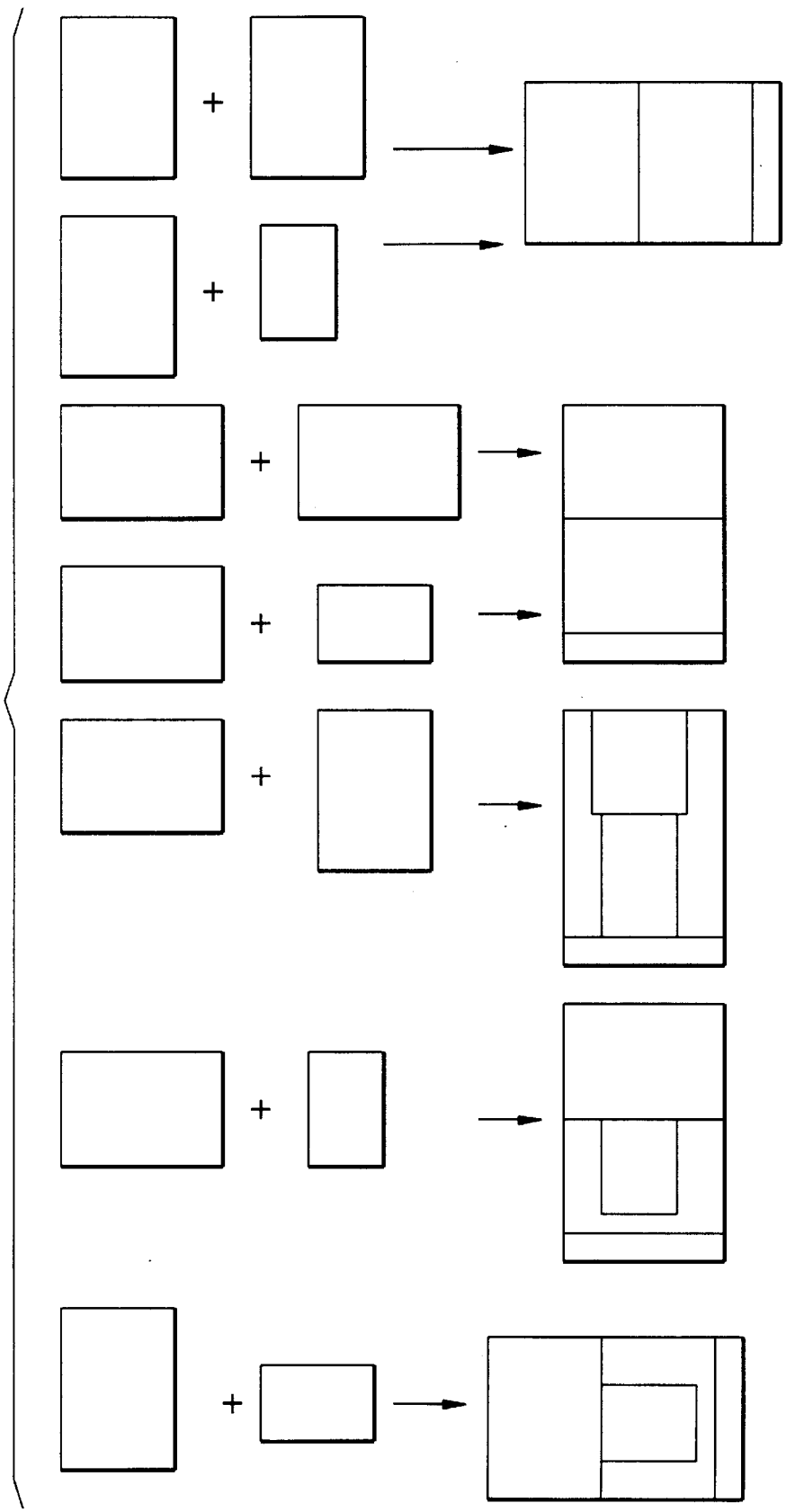
FIG. 8 depicts diagrammatically the various arrangements provided for two images on the same page of an editing medium.

It is obvious that each specific editing program can be more or less complex according to the requirements of the applications. For example, as depicted schematically in FIG. 8, when it is desired to edit two images per page of the editing medium, the editing module can first of all check the orientations of the two images and choose, when the orientations are identical, the orientation of the editing according to this orientation. When the cartridges have different orientations, the editing module according to the size of the images will edit the images with the orientation corresponding to the image with the largest size, as depicted schematically in FIG. 8.

The embodiment of the editing control device 40 has been depicted and described, taking into account only the number of images to be edited on one and the same page of the editing medium in order to simplify the explanations and the flow diagram depicted. However, as indicated previously, the digital medical imaging unit can edit images on three editing media of different sizes. Persons skilled in the art will therefore have to take into account this information entered before the insertion of the phosphor cartridge into the reading device. To do this, it will be necessary to add a control module for an area TL of the header of the file supplied by the reading device 20 and fulfilling the same role as the area TH; the area TL containing the information about size or format of the editing medium. This module will record the size of the medium, for example in an area Fedit(Id), entered by the operator when the information is present in the header of the image, and will prevent the modification of this area when no information has been entered This module can be placed for example just upstream or just downstream of the area TH verification module. In addition it will be possible to make provision, when the first image arrives in the editing control device 40, for the default loading of the area Fedit(Id) corresponding to an editing medium format for the patient Id, if the area TL of the first image has not been given. This can be effected by means of a loop analogous to that depicted in FIG. 4B, for example placed just upstream or just downstream of the loop depicted in FIG. 4B.

In a particularly advantageous embodiment, provision is also made for the possibility of adding by overlaying predetermined comments at each image. These comments will be chosen from amongst a predefined list, as depicted in FIG. 9, and the information is entered before the insertion of the cartridge into the reading device, for example with the bar code reader. The editing station will therefore be able, by overlaying, to dispose the comments at predetermined positions in the corresponding images and then edit the images with the overlaying of a comment. Since overlays are well known in the technique of imaging editing, it has not been deemed necessary to describe in any more detail the operation of the editing device.

Figure 4C:
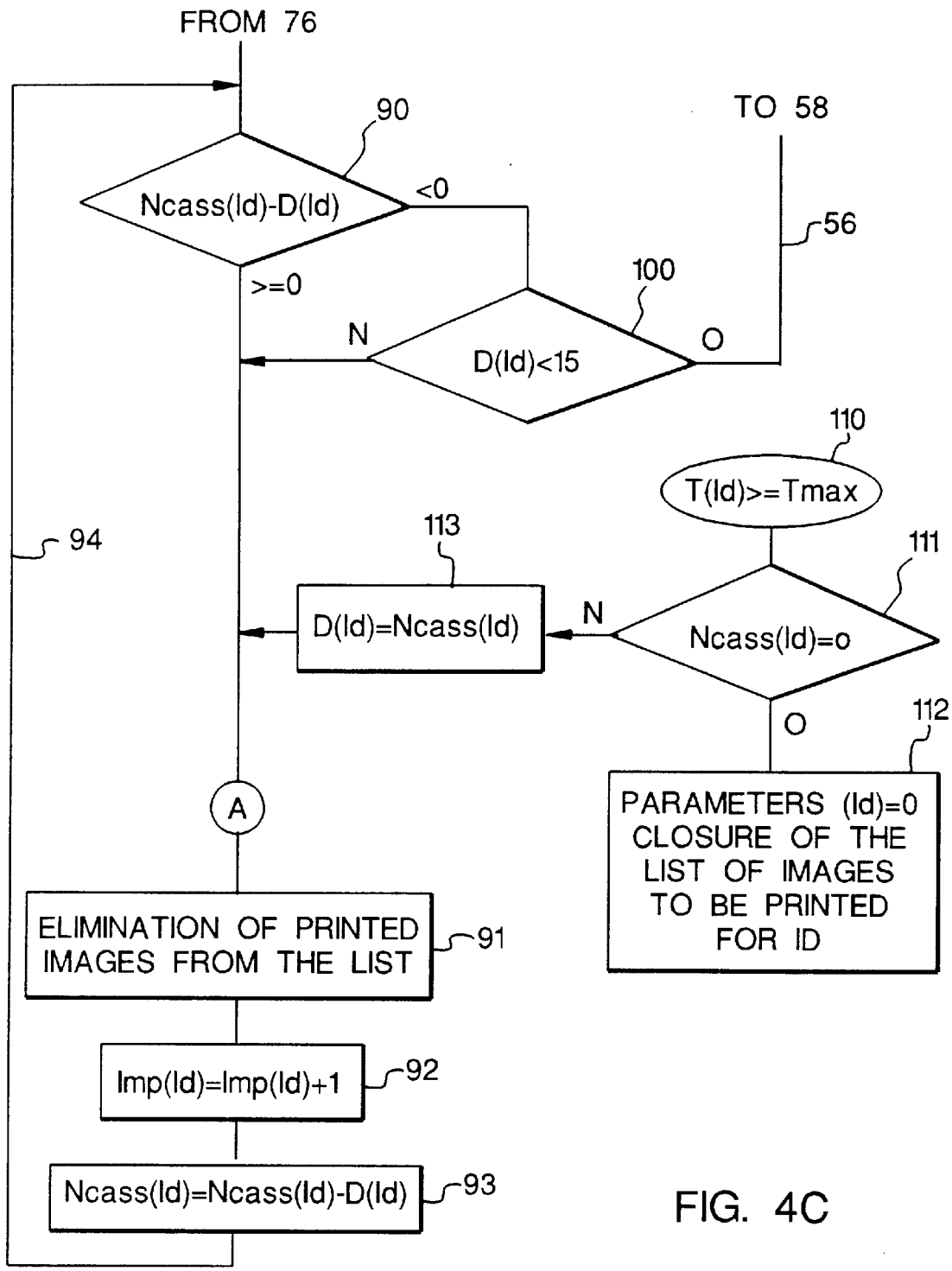
Figure 5A:
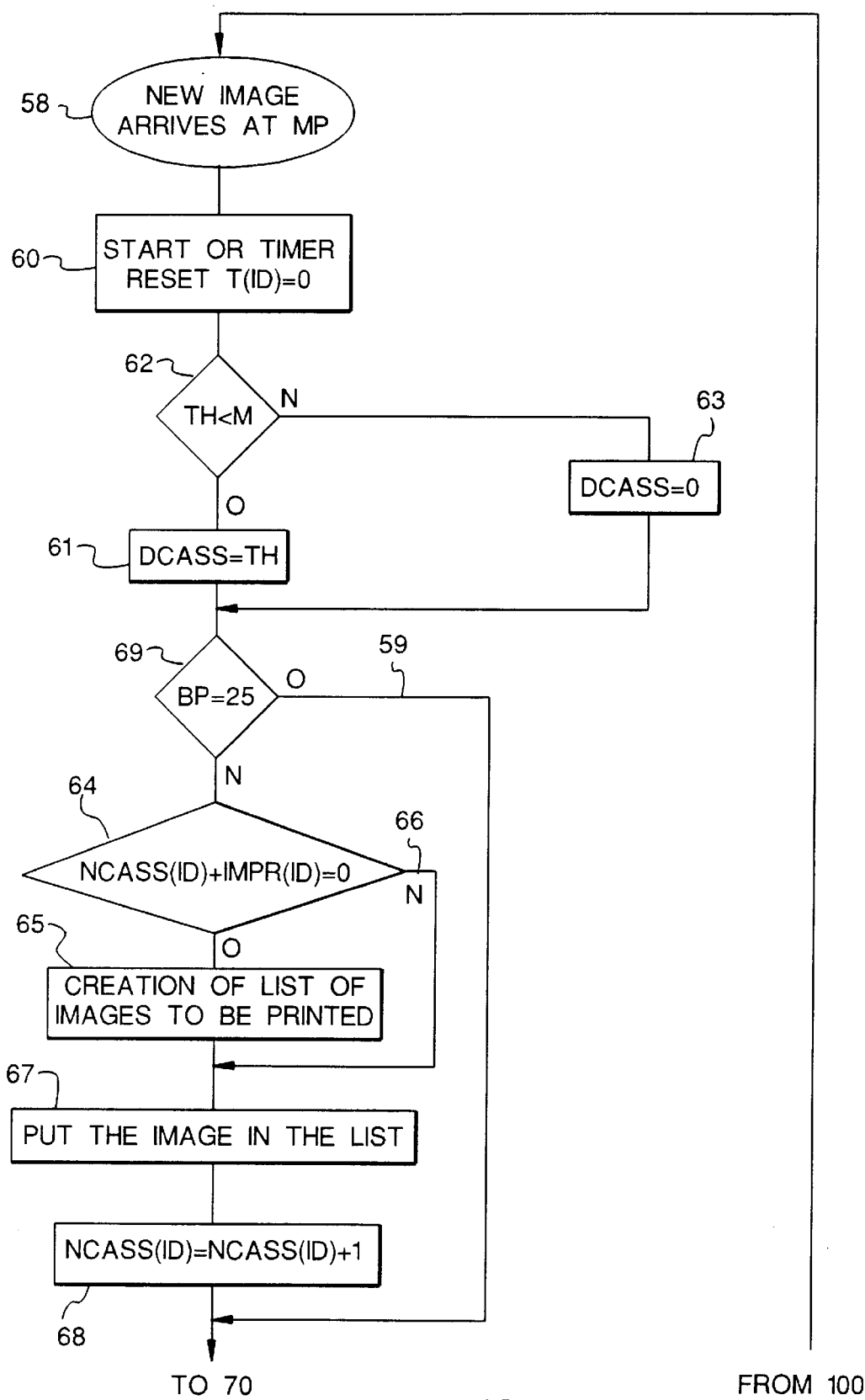
FIGS 5A to 5C depict diagrammatically another embodiment according to the invention.
Figure 5B:
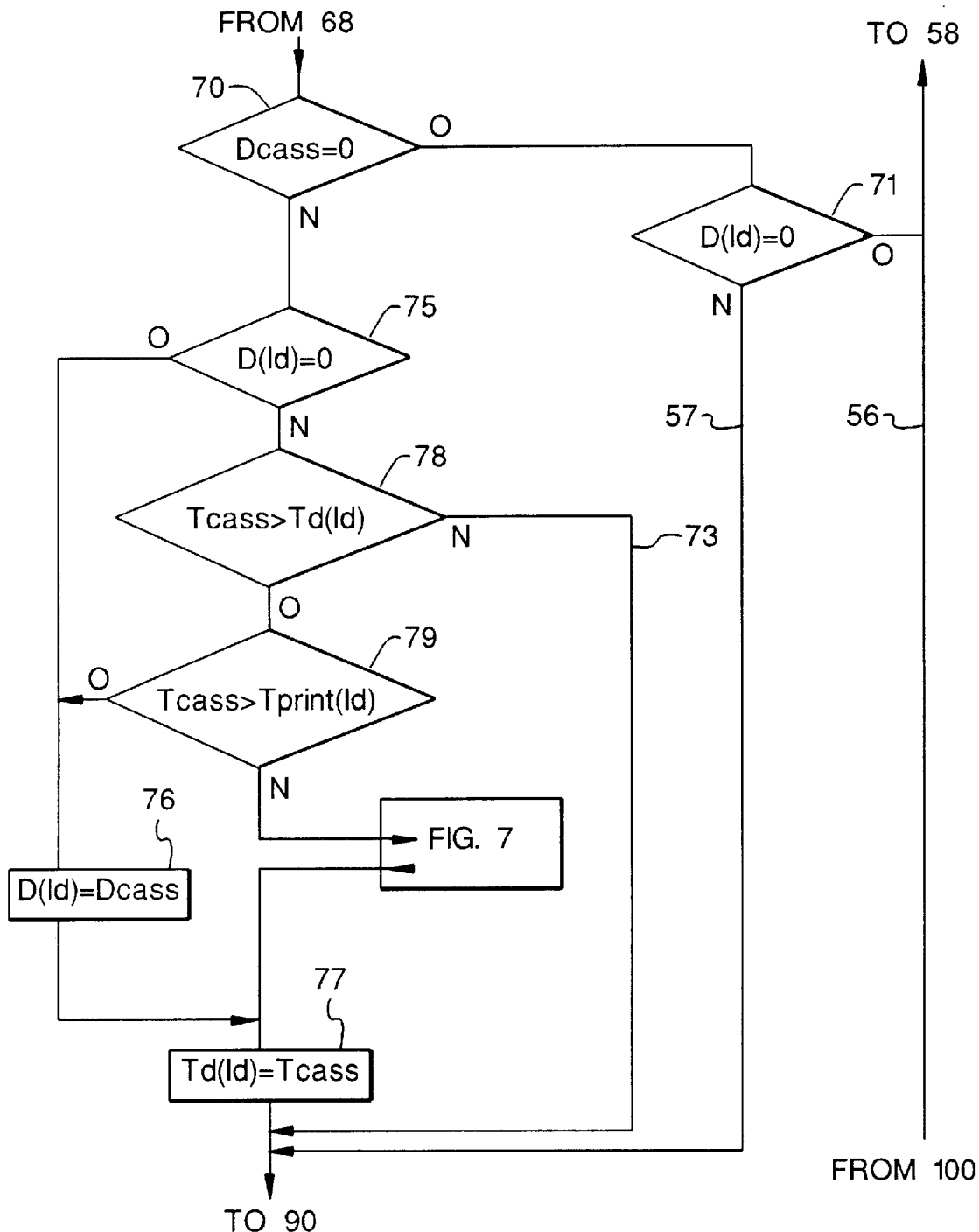
Figure 5C:
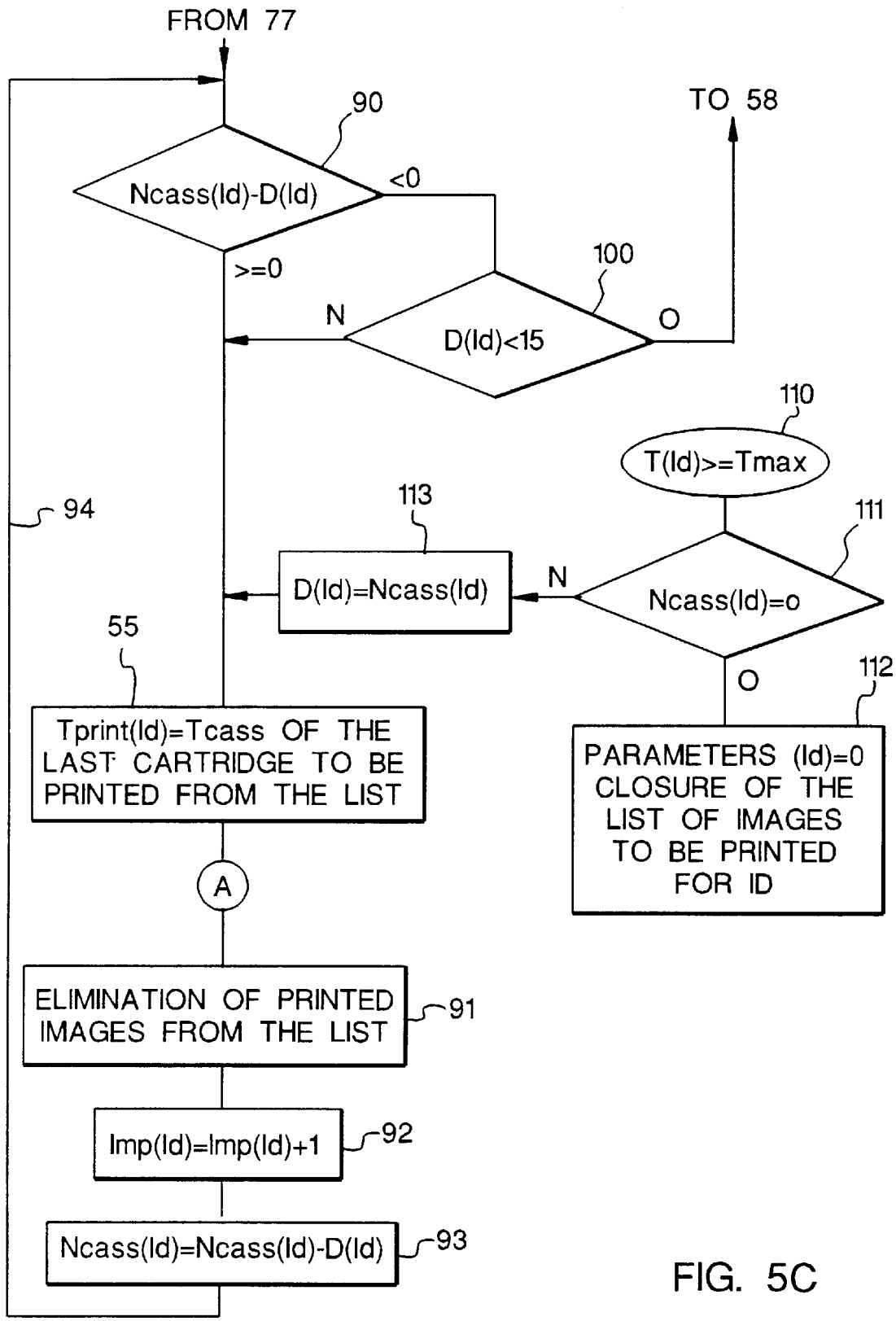

In another particularly advantageous embodiment depicted in FIGS. 5A to 5C, the phosphor cartridges no longer need to reach the reading device 20 strictly in the order of their entry. For this purpose, the operating flow diagram of the editing control device depicted in FIGS. 4A to 4C has been modified. The same references have been used for the circuits representing the same functions.

When it is desired to be able to edit the images correctly in spite of a reversal in the order of reading of the cartridges, it suffices to await the reading of the cartridge containing, in the area TH, the number of images to be edited per page of the editing medium. In addition, in order to allow, as in the embodiment described with reference to FIGS. 4A to 4C, a certain modification in the number of images edited per page of editing medium, the operating flow diagram has been modified in order to introduce supplementary checks. This is because, the cartridges having been inserted in the reader in any order, it will be necessary to check that the modification is indeed subsequent to the information which has already been used. To do this the moment when the number of images to be edited was supplied to the cartridge will be recorded in an area Td(Id). This information is available in Tcass of the header of the image file supplied by the Kodak device mentioned above. However, the disordering introduced into the cartridge batch may prevent editing in accordance with the desired modification.

As will be noted, FIG. 5A is identical to FIG. 4A and reference will be made to the description given with reference to FIG. 4A for an understanding of the present embodiment. It will also be noted that the only change between FIG. 5C and FIG. 4C lies in the introduction at 55 in an area Tprint(Id) of the time at which the last cartridge printed was read by the reading device 20; this information is situated in the area Tcass, supplied by the reading device 20 in the header of the image file. This information will make it possible to know whether the modification made to the number of images to be edited per page of editing medium is subsequent to or prior to the last cartridge printed.

A description will now be given, with reference to FIG. 5B, of the operation of the editing control device 40 modified so as to permit a certain degree of mixing of the cartridges. After having drawn up the list of images to be printed and counted the number of cassettes read, the editing control device 40 tests the value of Dcass. If Dcass is zero, which corresponds to the fact that no information relating to the number of images to be transferred to a single page of the editing medium has been entered, the editing control device 40 then tests the value of D(Id) at 71. When the editing control device 40 tests the first image, the value of D(Id) is zero since it has not yet been given. Because of this, the positive output of the test 71, D(Id)=0, sends back, by means of the line 56, the editing control device 40 to await the following image at 38, and this operation is renewed until a cartridge supplies the number of images to be edited per page of editing medium.

When the cartridge having the information relating to the number of images to be transferred to a single page of the editing medium finally arrives at the editing control device 40, the test at 70, Dcass=0, finally becomes negative. The editing control device 40 then tests at 75 the value of D(Id). The area which has not yet been given is zero. In this case, the editing control device 40 introduces at 76 the value of Dcass in the area D(Id) and then updates at 77 the area Td(Id) by transferring into this area the value of Tcass. This area Tcass of the header of the image file supplied by the control device mentioned above, contains the time of identification of the cartridge for which the value of the number of images to be edited per page of editing medium has been entered. This value is introduced into the area Td(Id).

Once the number of images to be edited per page of editing medium is known, the editing control device 40 can compare at 90 the number of images received from the reading device 20 with the number of images to be edited per page of editing medium and can continue the process as indicated previously in the description of the previous embodiment given with reference to FIG. 4C.

The following images received from the reading device generally do not contain any more information relating to the number of images to be edited per page of editing medium. In this case the value of Dcass is zero, and the editing control device 40, after having tested Dcass=0 at 70, tests the value of D(Id) at 71. This area, which was given previously, is no longer zero. The result of the test 71 is negative and, by virtue of the path 57, the editing control device 40 does not give the area Td(Id). The editing control device 40 once again compares at 90 the number of images received from the reading device 20 with the number of images to be edited per page of editing medium. When the editing control device 40 has received a sufficient number of images it causes editing in the manner indicated above with reference to FIG. 4C.

When a cartridge contains a new item of information relating to the number of images to be edited per page of editing medium, the test 70, Dcass=0, is negative. The result of the test 75, D(Id)=0, is also negative. The editing control device 40 then tests at 78 the time of identification Tcass of the current cartridge which has supplied the value of the number of images to be edited per page of editing medium compared with the time of identification Td(Id) of the cartridge which has supplied the value of the number of images to be edited per page of editing medium. When Tcass is prior to Td(Id), (Tcass<Td(Id)), the information concerning the number of images to be edited per page of editing medium is not taken into consideration since it was modified subsequently and the editing control device 40 is already in possession of this information. When Tcass is subsequent to Td(Id), (Tcass>Td(Id)), the editing control device 40 then tests at 79 the time of identification Tcass of the current cartridge which has supplied the value of the number of images to be edited per page of editing medium compared with the time Tprint(Id) corresponding to the last cartridge printed. When the identification time Tcass of the current cartridge which has supplied the value of the number of images to be edited per page of editing medium is subsequent to the time Tprint(Id), (Tcass>Tprint(Id)), corresponding to the last cartridge printed, the editing control device 40 takes account of the new number of images to be edited per page of editing medium by performing the operation 76, D(Id)=Dcass, then updates at 77 the identification time Td(Id) with the value Tcass of the current cartridge which has supplied the new value of the number of images to be edited per page of editing medium, checks at 90 the number of images to be edited compared with the new value of the number of images to be edited per page of editing medium, and if applicable performs the printing.

It is clear that, having regard to the test 75, 78 and 79, it will be possible, just at the positive output of the test 71, to introduce into the area D(Id) a very large default value, for example equal to 9, since in the editing module it is possible to present up to nine images per page of editing medium. This high value makes it possible to receive a large number of images without editing before receiving the information relating to the number of images to be transferred to a single page of the editing medium.

When the time of identification Tcass of the current cartridge which has supplied the value of the number of images to be edited per page of editing medium is subsequent to the time Tprint(Id), (Tcass<Tprint(Id)), corresponding to the last cartridge printed, the modification arrives after the printing of the images whose presentation it was deemed to modify. The editing control device 40 then controls the editing of the images in the list of images awaiting editing.

Figure 7:
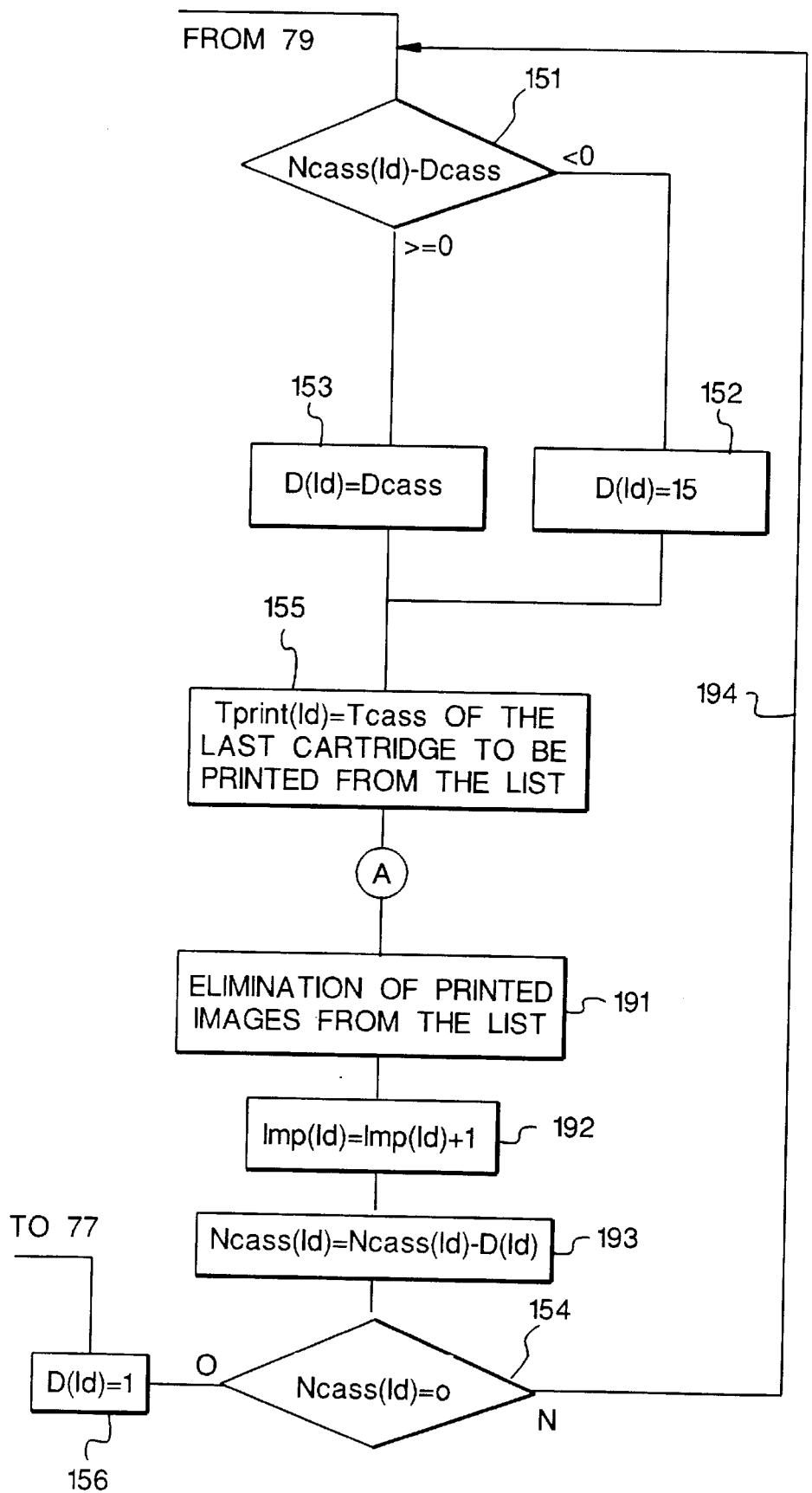
FIG. 7 depicts diagrammatically a possible flow diagram which can be used with the embodiment depicted in FIGS. 5A to 5C for editing the images contained in the list of images to be edited.

A description will now be given, with reference to FIG. 7, of the operation of the editing control device 40 for editing the waiting images. It is clear that any other algorithm could also be used. The editing control device 40, after having found that all the wishes of the operator cannot be taken into account since the cartridge arrives too late, tests at 151 the number of images awaiting editing compared with the new number Dcass of images to be edited on a page of the editing medium. When Ncass(ID)−Dcass is positive or zero, the editing control device 40 modifies at 153 the former value of D(Id) in order to transfer thereto the value of Dcass. If the result of the test 151 (Ncass(Id)−Dcass) is negative, the editing control device 40 modifies at 152 the former value of D(Id) in order to put therein the value 15. Then the area Tprint(Id) is given at 155 with the value of Tcass of the last cartridge in the printing list. Editing is then triggered by the operation A and then the printed images are removed from the list at 191, the printing counter Imp(Id) is incremented by one unit at 192, the number of images to be edited is decremented at 193 by the value of D(Id). It is checked that all the images have been printed at 154 by a test Ncass(Id)= O. If there are still images to be printed, there is a loop-back, through the path 194, to the test 151 Ncass(Id)Dcass until there are no longer any images waiting. At this moment, the value of D(Id) is forced to 1 in order to edit any images relating to the patient Id which might still remain in the loader 22 or in the reading device 24. These images will be edited with one image per page of editing medium.

The invention has been described in detail with particular reference to certain preferred embodiments thereof, but it will be understood that variations and modifications can be effected within the spirit and scope of the invention.

PARTS LIST

10 entry station
12 keyboard
14 printer
16 means
18 data capture device
19 storage circuit
20 reading device
22 automatic feed dispenser
24 processing unit
30 editing station
40 automatic editing control device
50 laser printer

What is claimed is:

1. Digital medical imaging unit for automatically editing, on a page of an editing medium, radiographic images recorded on first recording media, comprising:

(a) an entry means for unequivocally codifying information relating to a given patient (Id), (b) a device for reading each first recording medium so as to obtain a digital radiographic image of the information carried by the first recording medium, (c) a device for identifying each first recording medium introduced into the reading device, (d) a correlation means for unequivocally associating each first recording medium with a given patient, (e) a unit for processing the digital radiographic images, (f) an editing means designed to reproduce, on an editing medium, at least one digital image modified by the processing unit, characterized in that it comprises:

(g) a means of entering an item of editing information in order, before the reading of a first recording medium containing a radiographic image, to associate with one and the same page of an editing medium a plurality of first recording media with a view to editing several radiographic images of a given patent on one and the same page of an editing medium, (h) a counter of processed images (Ncass(Id)) so as to edit the plurality of digital radiographic images associated with one and the same page of the editing medium only after receipt of the number of images corresponding to the plurality of radiographic images to be edited and (i) a time counter with a maximum value Tmax for triggering said editing means to edit images when images relating to said given patient have not been received for a time period Tmax.

2. Unit according to claim 1, in which the editing information entry means comprises a means for choosing the dimension of the editing medium amongst a finite list of given dimensions.

3. Unit according to claim 1, in which the editing information entry means comprises a means for choosing the number of digital radiographic images which the printer edits on one and the same page of the editing medium.

4. Unit according to claim 1, in which the editing information entry means comprises a means for associating predefined information with at least one of the digital radiographic images to be edited.

5. Unit according to claim 1, comprising a means (D(Id)) for enabling, before editing, a modification of the number of images to be edited on one and the same page of the editing medium.

6. Method for automatically using a digital medical imaging unit comprising:

(a) an entry means for codifying information relating to a patient whose digital radiographic images are to be produced on a first recording medium, (b) a device for reading each first recording medium so as to obtain a digital representation of the radiographic image carried by the first recording medium, (c) a device for identifying each first successive recording medium introduced into the reading device, (d) a unit for processing digital radiographic images, (e) an editing means designed to reproduce, on an editing medium, at least one digital image processed by the processing unit, and in which:

(1) the information relating to the patient are codified unequivocally, (2) each first recording medium is associated unequivocally with a given patient, (3) the radiographic image recorded on a first recording medium is digitized by means of the reading device and the digital representation of this radiographic image is transmitted to the processing unit, (4) the digital image is modified, and (5) the modified digital image is edited on the editing medium by virtue of the editing means, a method characterized in that:

before the digitization of the image recorded on the first medium, an item of editing information is entered controlling the processing unit so as to automatically edit on one and the same page of an editing medium a plurality of digital radiographic images, the said processing unit commencing editing only after receipt of the number of images corresponding to the plurality of digital images determined by the item of editing information corresponding to the plurality of digital images which correspond to a given patient and which are to be edited on one and the same page of the editing medium; and when a time counter with a maximum value Tmax determines that images relating to said patient have not been received for a time period Tmax.

7. Digital medical imaging unit for automatically editing, on a page of an editing medium, radiographic images recorded on first recording media, comprising:

(a) entry means for unequivocally codifying information relating to a given patient, (b) reading means for reading each first recording medium so as to obtain a digital radiographic image of the information carried by the first recording medium, (c) identifying means for identifying each first recording medium introduced into the reading means, (d) correlation means for unequivocally associating each first recording medium with a given patient, (e) editing means designed to reproduce, on an editing medium, at least one digital image provided by the reading means, (f) capture means for entering an item of editing information in order, before the reading of a first recording medium containing a radiographic image, to associate with one and the same page of an editing medium a plurality of first recording media corresponding to a given patient with a view to editing several radiographic images on one and the same page of an editing medium, (g) counter means for counting the radiographic images provided by the reading means so as to edit the plurality of digital radiographic images associated with a given patient and with one and the same page of the editing medium only after receipt of the number of images corresponding to the plurality of radiographic images to be edited on such medium; and (h) a time counter with a maximum value Tmax for triggering said editing means to edit images when images relating to said given patient have not been received for a time period Tmax.

8. Method for automatically using a digital medical imaging unit comprising:

(a) entry means for codifying information relating to a patient whose digital radiographic images are to be produced on a first recording medium, (b) reading means for reading each first recording medium so as to obtain a digital representation of the radiographic image carried by the first recording medium, (c) identifying means for identifying each first successive recording medium introduced into the reading device, (d) editing means designed to reproduce, on an editing medium, at least one digital image processed by the processing unit, method comprising the steps of:

(1) unequivocally codifying the information relating to the patient, (2) unequivocally associating each first recording medium with a given patient, (3) digitizing by means of the reading means the radiographic image recorded on a first recording medium and transmitting to the editing means the digital representation of this radiographic image, (4) before the digitization of the image recorded on the first medium, entering an item of editing information for controlling the editing means so as to automatically edit on one and the same page of an editing medium a plurality of digital radiographic images corresponding to a given patient, said editing means commencing editing only after receipt of the number of images determined by said item of editing information and corresponding to the plurality of digital images to be edited on one and the same page of the editing medium, and (5) editing the modified digital image on the editing medium by virtue of the editing means; when a time counter with a maximum value Tmax triggers said editing means when images relating to said patient have not been received for a time Tmax.

* * * * *